United States Patent [19]

Murchison et al.

[11] 4,151,190

[45] Apr. 24, 1979

[54] PROCESS FOR PRODUCING $C_2$–$C_4$ HYDROCARBONS FROM CARBON MONOXIDE AND HYDROGEN

[75] Inventors: Craig B. Murchison, Midland; Dewey A. Murdick, Sanford, both of Mich.

[73] Assignee: The Dow Chemical Company, Midland, Mich.

[21] Appl. No.: 814,761

[22] Filed: Jul. 11, 1977

Related U.S. Application Data

[63] Continuation-in-part of Ser. No. 688,861, May 21, 1976, abandoned.

[51] Int. Cl.$^2$ ............................................. C07C 1/04
[52] U.S. Cl. ........................ 260/449 R; 260/449 M; 260/449.6 M; 260/449.6 R; 252/439; 252/444; 252/447; 252/454; 252/461; 252/458; 252/465
[58] Field of Search ................... 260/449 R, 449.6 R, 260/449 M, 449.6 M

[56] References Cited

U.S. PATENT DOCUMENTS

| | | | |
|---|---|---|---|
| 2,284,468 | 5/1942 | Burk et al. ...................... | 260/449.6 |
| 2,490,488 | 12/1949 | Stewart ........................... | 260/449 R |
| 2,960,518 | 11/1960 | Peters ............................. | 260/449.6 |
| 2,973,384 | 2/1961 | Hayashi et al. ................. | 260/449.6 |
| 3,240,698 | 3/1966 | Leak et al. ...................... | 260/449 R X |
| 3,511,624 | 5/1970 | Humphries et al. ............. | 260/449 M X |
| 3,549,556 | 12/1970 | Dienes ............................. | 260/449 M |
| 3,842,113 | 10/1974 | Ichikawa et al. ................ | 260/449 R |
| 3,842,121 | 10/1974 | Ichikawa et al. ................ | 260/449 R |
| 3,927,999 | 12/1975 | Child et al. ..................... | 260/449 M |
| 3,928,001 | 12/1975 | Child et al. ..................... | 260/449 M |
| 3,941,819 | 3/1975 | Vannice et al. ................. | 260/449 R |
| 4,032,556 | 6/1977 | Banks .............................. | 260/449.6 M |

FOREIGN PATENT DOCUMENTS 593940 10/1947 United Kingdom .................. 260/449.6

*Primary Examiner*—Howard T. Mars
*Attorney, Agent, or Firm*—G. R. Plotecher

[57] ABSTRACT

Hydrocarbons of two to four carbon atoms are prepared by an improved Fischer-Tropsch process, the improvement comprising the use of a catalyst comprising:

(A) at least one material selected from the group consisting of the sulfide, oxide or metal of Mo, W, Re, Ru, Ni and Pt;
(B) at least one material selected from the group consisting of the hydroxide, oxide or salt of Li, Na, K, Rb, Cs, Mg, Ca, Sr, Ba and Th; and
(C) a support.

The catalyst demonstrates good $C_2$–$C_4$ selectivity, is resistant to sulfur poisoning and is regenerable.

30 Claims, No Drawings

PROCESS FOR PRODUCING C₂-C₄ HYDROCARBONS FROM CARBON MONOXIDE AND HYDROGEN

CROSS-REFERENCE TO RELATED APPLICATION

This application is a continuation-in-part of application Ser. No. 688,861, filed May 21, 1976 now abandoned.

BACKGROUND OF THE INVENTION

1. Field of the Invention

This invention relates to an improved process for the production of hydrocarbons from carbon monoxide and hydrogen. In one aspect, this invention relates to a catalyst for use in the process to produce hydrocarbons containing two to four carbon atoms.

2. Description of the Prior Art

The art contains many examples of metals known to be useful in reacting carbon monoxide with hydrogen to produce a variety of compounds — both hydrocarbons and oxygenated compounds. These metals include, among others, Mo, W, Th, Ru, Re, Pt, Ni, Co, and Fe. It is upon the last two of these metals that most commercial experience is based. In what has come to be called the Fischer-Tropsch synthesis, carbon monoxide and hydrogen are reacted over an iron or cobalt catalyst to produce saturated and unsaturated hydrocarbons and oxygenated compounds containing from about one to as many as one thousand carbon atoms. The hydrocarbons can be aliphatic, alicyclic, or aromatic. Commercial utilization of this Synthesis prior to 1950 was accomplished largely in Germany and is summarized in Storch, Columbic, and Anderson: *The Fischer-Tropsch and Related Synthesis*, John Wiley and Sons, New York 1951.

The following references are illustrative of the prior art and are helpful to an understanding of Applicant's invention:

Schultz, John Floyd, "Noble Metals, Molybdenum and Tungsten in Hydrocarbon Synthesis", by J. F. Schultz, F. S. Carn, and R. B. Anderson. (Washington) *U.S. Dept. of the Interior, Bureau of Mines Report* 6974 (1967).

Anderson, R. B., "Fischer-Tropsch Synthesis", by R. B. Anderson, B. Seligman, J. F. Schultz, R. Kelly, and M. A. Elliott. *Industrial and Engineering Chemistry*, Vol. 44, No. 2 (1952).

West German Pat. No. 2,343,032 "Process for Controlling Fischer-Tropsch Synthesis", Inventor: Dr. Mark Eberhard Dry, Priority Date: Sept. 5, 1972.

Mills, G. Alex, and Fred W. Steffgen, "Catalytic Methanation", *Catalysts Review*, Vol. 8, pages 159–210 (1973).

Dry, M. E., T. Shingles, L. J. Boshoff, and G. J. Oostehurzen, "Heats of Chemisorption on Promoted Ion Surfaces and the Role of Alkali in Fischer-Tropsch Synthesis". *Journal of Catalysis*, Vol. 15, pages 190–199 (1969).

Pichler, Helmet and Annemarie Hector, "Carbon Monoxide-Hydrogen Reactions", *Encyclopedia of Chemical Technology* Vol. 4 (2nd Edition) pages 446–489.

Weitkamp, A. W., Herman S. Seelig, Norman J. Bowman, and William E. Katy, "Products of the Hydrogenation of Carbon Monoxide Over an Iron Catalyst", *Industrial and Engineering Chemistry*, Vol. 45, No. 2, pages 343–367 (1953).

U.S. Pat. No. 2,490,488 "Hydrocarbon Synthesis Catalyst", Inventor: S. Grant Stewart; Issued: Dec. 6, 1949.

As mentioned above, the most extensive commercialization of the Fischer-Tropsch synthesis has been with the use of either an iron or a cobalt catalyst. Such catalysts produce a potpourri of saturated and unsaturated aliphatic and aromatic hydrocarbons as well as oxygenated compounds which for the most part contain more than four carbon atoms. The cracking of these compounds to produce ethylene and/or propylene is not very efficient. For this purpose the desired compounds are ethane, propane, and the various isomers of butane and butene. In addition sulfur impurities such as hydrogen sulfide, carbonyl sulfide, or any other sulfur compound deactivate iron and cobalt catalysts in concentrations as low as 0.1 ppm.

Schultz has shown molybdenum to have some sulfur resistance. His work was directed toward the development of an efficient catalyst to produce methane from carbon monoxide and hydrogen and he was reasonably successful. However, methane is not the preferred feedstock for the production of ethylene and/or propylene. For the present purposes, the catalysts of iron and cobalt produce molecules containing too many carbon atoms, and the catalysts tested by Schultz produce molecules containing too few carbon atoms.

The present invention relates to a process which produces molecules containing a more desirable number of carbon atoms for use as ethylene cracker feedstocks. Typical catalysts in use today for this reaction require lowering of the concentration of sulfur impurities to approximately 0.1 ppm. Since it is expensive to decrease the concentration of sulfur impurities to a level of approximately 0.1 ppm, development of a catalyst usable at a higher concentration would result in considerable savings in investment and operating costs in a commercial facility. The catalyst of the present invention can be employed with a higher concentration of sulfur impurities in the feedstock. The catalyst of the present invention does not require precious metals and is capable of sustained operation at a hydrogen to carbon monoxide ratio of one to stimulate formation of the saturated and unsaturated hydrocarbons containing from two to four carbon atoms.

Objects

It is an object of the present invention to effect an improved yield of hydrocarbons containing two to four carbon atoms in their synthesis from carbon monoxide and hydrogen. Another object of this invention is to prepare hydrocarbons from a feedstock containing levels of sulfur impurities higher than could previously be tolerated in processes of this type. A further object of the present invention is to provide a process selective to the production of hydrocarbons alone. A still further object of the present invention is to provide a commercially feasible process for producing hydrocarbons.

SUMMARY OF THE INVENTION

These and other objects of this invention are obtained by an improved process for producing hydrocarbons from contacting carbon monoxide and hydrogen at reactive conditions, the improvement comprising increasing the yield of the saturated and unsaturated hydrocarbons containing from two to four carbon atoms by contacting the carbon monoxide and hydrogen with a catalyst comprising:

(A) between about 1 percent and about 95 percent by weight based upon the weight of the catalyst of at least one material selected from the group consisting of the metal, oxide or sulfide of molybdenum, tungsten, rhenium, ruthenium, nickel and platinum;

(B) between about 0.05 percent about 50 percent by weight based upon the weight of the catalyst of at least one material selected from the group consisting of the hydroxide, oxide or salt of lithium, sodium, potassium, rubidium, cesium, magnesium, calcium, strontium, barium and thorium; and (C) at least about 1 percent by weight based upon the weight of the catalyst of a support.

The catalyst of this invention is advantageous for producing hydrocarbons of two to four carbon atoms but is particularly advantageous for producing hydrocarbons of two or three carbon atoms, and especially advantageous for producing hydrocarbons of two carbon atoms.

DETAILED DESCRIPTION OF THE INVENTION

The carbon monoxide required for the process can be obtained from any carbon source, such as from the degradation of coal or of high molecular weight hydrocarbon residuals. In the case of a carbon-supported sulfur-resistant catalyst species of the invention (the metals molybdenum, tungsten, and their oxides and sulfides), the feed can contain substantial quantities of sulfur impurities without irreversibly affecting either the selectivity or activity of the catalyst. The molar ratio of hydrogen to carbon monoxide ranges generally from at least about 0.25 and preferably about 0.5 to an upper limit of about 4.0 and preferably about 1.5.

The catalyst used in the practice of the invention is typically a three-component catalyst. The first component is at least one material selected from the group consisting of the sulfide, oxide or metal of molybdenum, tungsten, rhenium, ruthenium, nickel and platinum. "At least one" means that the first component can consist of two or more members of this enumerated group, including such combinations as the sulfide, oxide and metal of one element, or the oxides or sulfides of different elements, or the sulfide of one element and the oxide of another, or different oxides or sulfides, if any, of the same element, etc. As used herein, "sulfide" includes those compounds that have oxygen and sulfur directly attached to the same metal atom, such as O-Mo-S. This first component is present in an amount, based upon the weight of the catalyst, of at least about 1 and preferably at least about 10 weight percent with an upper limit of about 95 and preferably about 50 weight percent. A preferred first component is at least one material selected from the group consisting of the sulfide, oxide or metal of molybdenum and tungsten. An especially preferred first component is at least one material selected from the group consisting of the sulfide, oxide or metal of molybdenum.

The second component is at least one material selected from the group consisting of the hydroxide, oxide or salt or lithium, sodium, potassium, rubidium, cesium, magnesium, calcium, strontium, barium and thorium. "At least one" means that the second component can consist of two or more members of this enumerated group, including such combinations as the hydroxide, oxide and salt of one element, or the hydroxides, oxides or salts of different elements, or the hydroxide of one element and the oxide of another, or different oxides or salts, if any, of the same element, etc. The second component is present in an amount, based upon the weight of the catalyst, of at least about 0.05 and preferably at least about 0.5 weight percent with an upper limit of about 50 and preferably about 10 weight percent. A preferred second component is at least one material selected from the group consisting of the hydroxide, oxide or salt of lithium, sodium, potassium, rubidium and cesium. An especially preferred second component is at least one material selected from the group consisting of the hydroxide, oxide or salt of potassium.

The third component is a support of any physical form, such as granules, beads, extrudates, etc. Exemplary supports include: alumina, silica, carbon, zirconia, magnesia, etc. The carbon supports include saran carbon beads. These beads are a substantially dust and contaminant-free carbonized product made from vinylidene chloride polymers and, when loaded with the first two components of this invention's catalyst, constitute a novel Fischer-Tropsch catalyst having a pronounced selectivity for producing $C_2$–$C_4$ hydrocarbons. For more detail regarding these beads, see "The Absorption Characteristics of Polyvinylidene Chloride Carbon" by A. N. Ainscough, D. Dollimore, G. R. Heal in Carbon 11, 189–197 (1973). Based upon the weight of the catalyst, the support comprises at least about 1 percent of the catalyst and generally not more than about 98.95 percent of the catalyst. Preferably, the support comprises at least about 50 weight percent, and most preferably at least about 80 weight percent, of the catalyst.

Although any number of materials can serve as a support, alumina and carbon supports are preferred, with the latter especially preferred. The activity and selectivity of a catalyst comprising a carbon support is essentially equivalent to that comprising an alumina support. The activity of the catalyst is a measure of its ability to promote the formation of hydrocarbon molecules without regard to the number of carbon atoms in a molecule. The selectivity of the catalyst is a measure of its ability to promote the formation of hydrocarbon molecules containing the desired number of carbon atoms.

Components of this invention's catalyst can be present per se or as an integral part of one another or as a combination thereof. Illustrative of components being present as an integral part of one another, carbon supports prepared from coconut often contain relatively small (based on the weight of the support) amounts of alkali metal oxides and/or hydroxides.

Preferred species of this invention's catalyst have as a first component at least one material selected from the group consisting of the sulfide, oxide or metal of molybdenum and tungsten. More preferred species have as a first component at least one material selected from the group consisting of the sulfide, oxide or metal of molybdenum and tungsten and as a second component at least one material selected from the group consisting of the hydroxide, oxide or salt of lithium, sodium, potassium, rubidium and cesium. Still more preferred species have as a first component at least one material selected from the group consisting of the sulfide, oxide or metal of molybdenum and tungsten, as a second component at least one material selected from the group consisting of the hydroxide, oxide or salt of lithium, sodium, potassium, rubidium and cesium, and as a third component an alumina or carbon support. or carbon support. Especially preferred species have as a first component at least one material selected from the group consisting of the sulfide, oxide or metal of molybdenum, as a second component at least one material selected from the group consisting of the hydroxide, oxide or salt of potassium, and as a third component a carbon support.

The presence of sulfur impurities in the feed alters the selectivity and activity of the catalyst after a period of time. Methane production is increased with a consequential decrease in production of hydrocarbons containing two or more carbon atoms. The sulfides and oxides of molybdenum and tungsten have been found resistant to poisoning by sulfur impurities. Regeneration of these sulfur resistant catalysts can be accomplished by treatment with hydrogen at about 15 psia and 400° C.-600° C. for about sixteen to forty-eight hours. Such treatment of a sulfur resistant catalyst restores the catalyst's activity and selectivity to its initial levels.

Reactive (process) conditions can vary over a rather broad range. The pressure can vary from about 15 psia to about 2000 psia. The preferred pressure is generally between about 200 and about 1000 psia. The reaction temperature ranges from at least about 250° C. and preferably about 375° C. to an upper limit of about 500° C. and preferably about 425° C.

The following examples should be considered illustrative of the surprising results obtainable with the invention and should not be construed as limiting of the invention. Unless otherwise indicated, all parts and percentages are by weight.

Specific Embodiments

Apparatus and Procedure

In preparation of a catalyst, supports were impregnated by a technique known as the incipient wetness technique. Water-soluble salts of active components of the catalyst and a support were chosen. A quantity of water which a catalyst support will adsorb is known as its pore volume. According to the desired catalyst loading, a quantity of the soluble salts was dissolved in water approximately equal to the pore volume of the support. The support was then immersed in the water which it absorbed completely. A wet cake was formed. The wet cake was first air-dried at room temperature for sixteen to twenty-four hours. It was then placed in an oven and heated at a rate of between about 0.4° C. and about 1.8° C. per minute in the presence of air or nitrogen to a final temperature dependent upon the type of support. Carbon supports were heated to between about 300° C. and about 400° C. Alumina supports were heated to between about 500° C. and about 650° C. Both supports were held at this final temperature for about six hours before being allowed to cool slowly to room temperature.

In Examples 1 through 7 an apparatus was utilized which included in sequential order three high-pressure gas bottles, a manifold, and five reactors each equipped on the downstream side with a fine metering valve and a rotameter through a sampling manifold to a gas chromatograph. The first bottle contained a mixture of hydrogen and carbon monoxide in a one to one molar ratio. The second bottle contained hydrogen and carbon monoxide in the same ratio but also contained carbonyl sulfide as a doped sulfur impurity. The third bottle contained hydrogen alone. Each bottle was independently connected to the manifold. The manifold was constructed such that any of the three bottles could be used either to feed all five reactors simultaneously, or to feed any one of the five alone, or to feed any combination of the reactors. Through the sampling manifold, the product of each reactor could be piped to the gas chromatograph for analysis.

The apparatus permitted reacting carbon monoxide and hydrogen in the presence of as many as five different catalysts under the same conditions. Before each run, catalyst was loaded in the reactors to be used and heated to 350° C. over a four-hour period in the presence of hydrogen. The hydrogen flow and a temperature of 350° C. were maintained for sixteen more hours. Then the catalyst was raised to a final temperature over a four-hour period. The final temperature was dependent upon the support as detailed above. This final temperature was held for sixteen to forty-eight hours. The outlet temperature of each reactor in use was maintained by the use of a hot air stream. The reactors were then lowered to operating temperature in the presence of hydrogen. Next, feed from the high-pressure gas bottle containing hydrogen and carbon monoxide was allowed to flow through the manifold to the reactor(s) being utilized. Pressure, flow, and temperature were adjusted to operating values.

The catalyst used in several runs was poisoned with a sulfur impurity and then reduced with hydrogen to determine its ability to be regenerated. This was the case in Examples 6, 7, 8, and 9, where, after a time period sufficient to establish the performance of the catalyst, the feed was switched from the bottle containing pure hydrogen/carbon monoxide to the bottle containing hydrogen/carbon monoxide with a sulfur impurity. After the effect on the catalyst of this impurity had been determined by reference to the carbon monoxide conversion and the product hydrocarbon distribution, the feed containing the impurity was shut off. For sixteen hours hydrogen was allowed to flow through the reactors which had been heated to a temperature between about 500° C. and about 600° C. The feed of pure hydrogen/carbon monoxide was restored for a period of time sufficient to determine the performance of the catalyst. The feed was then shut off and while they cooled to ambient temperature the reactors were purged with hydrogen.

In Example 2, the gas bottle containing hydrogen and carbon monoxide was used exclusively. After a period of time sufficient to establish the performance of each of the four catalysts, the feed was shut off. The reactors were purged with hydrogen while cooling to ambient temperature.

Subscripts (e.g. the 1 in $C_1$, etc.) in all examples indicate the number of carbon atoms. All hydrocarbon analyses are given in carbon mole percent in all examples. "Carbon mole percent" is defined as one hundred times the moles of carbon present in a hydrocarbon fraction divided by the total moles of carbon in product hydrocarbon. If one mole of ethane and one mole of ethylene are found in the $C_2$ fraction, this is counted as four moles of carbon. The term "product hydrocarbon" excludes any carbon dioxide produced. Unless otherwise indicated, molybdenum concentrations are reported as $MoO_3$ equivalents and potassium concentrations are reported as $K_2O$ equivalents.

EXAMPLE 1

Using the above catalyst, procedures, and apparatus, the following run was made to demonstrate the effect of the concentration of the second component of the catalyst upon product selectivity. For all runs the first component of the catalyst was molybdenum trioxide which was present in a concentration of 10 weight percent on saran carbon beads. In Runs 1B and 1C, the second component of the catalyst was potassium hydroxide. Reaction conditions are summarized below.

Temperature; 400° C.
Pressure 315 psia
Volume Hourly Space Velocity 300 hr$^{-1}$ The volume hourly space velocity is an indirect measure of the contact time between the catalyst and reactants. It is calculated by dividing the combined volume rate of flow of the reactants by the volume of the catalyst.

The catalyst of Run 1A contained no alkali, that of Run 1B contained 2.02 percent alkali (calculated as $K_2O$), and that of Run 1C contained 4.42 percent alkali (calculated as $K_2O$).

PRODUCT HYDROCARBON DISTRIBUTION

|  | Run 1A | Run 1B | Run 1C |
| --- | --- | --- | --- |
| $C_1$ Hydrocarbons | 70.6 | 53.8 | 37.5 |
| $C_2$ Hydrocarbons | 22.4 | 28.1 | 30.8 |
| $C_3$ Hydrocarbons | 6.2 | 13.3 | 21.3 |
| $C_4$ Hydrocarbons | 0.8 | 3.6 | 7.3 |
| $C_5$ Hydrocarbons | 0 | 1.2 | 3.2 |
| $C_6$ Hydrocarbons | 0 | 0 | 0 |

Note the increased yield in $C_2$ and higher hydrocarbons as the alkali concentration increases from Run 1A to Run 1C. These data show the surprising and significant increase in hydrocarbons containing from two to four carbon atoms available through the invention.

EXAMPLE 2

The following runs were made at constant pressure, temperature, and volume hourly space velocity. Molybdenum trioxide, the first component of the catalyst, was utilized on saran carbon beads for all runs. The second component of the catalyst, the alkali metal carbonate, was different for each reactor. The apparatus of Example 1 was used. Saran carbon beads were loaded with approximately 10 weight percent $MoO_3$ and, in each case, an equimolar amount of the respective carbonate according to the Apparatus and Procedure Section. The loading is summarized below:

| Second Component (Alkali Carbonate) | Millimoles Alkali Carbonate | Weight Percent Alkali (Calculated as alkali oxide) |
| --- | --- | --- |
| $Na_2CO_3$ | 5.23 | 1.19 |
| $K_2CO_3$ | 5.26 | 2.02 |
| $Rb_2CO_3$ | 5.14 | 4.39 |
| $Cs_2CO_3$ | 5.20 | 6.67 |

Reaction conditions for each of the four runs were:
Temperature; 400° C.
Pressure; 315 psia
Volume Hourly Space Velocity; 300 hr$^{-1}$ Run 1A which utilized only the first component of the catalyst, is reproduced below for comparison purposes. Analysis of the product hydrocarbons revealed them to be composed of:

|  | Run 1A (First Component only[1]) | Run 2 (Second Component Utilized)[1] | | | |
| --- | --- | --- | --- | --- | --- |
|  |  | $Na_2CO_3$ | $K_2CO_3$ | $Rb_2CO_3$ | $Cs_2CO_3$ |
| $C_1$ Hydrocarbons | 70.6 | 57.1 | 54.5 | 55.0 | 58.1 |
| $C_2$ Hydrocarbons | 22.4 | 27.9 | 28.7 | 30.5 | 27.3 |
| $C_3$ Hydrocarbons | 6.2 | 12.3 | 12.0 | 11.3 | 12.7 |
| $C_4$ Hydrocarbons | 0.8 | 2.7 | 3.5 | 3.2 | 1.9 |
| $C_5$ Hydrocarbons | 0 | 0 | 1.3 | 0 | 0 |

[1] All runs made with the catalyst on a saran carbon support.

These data show that the carbonates of Na, K, Rb, and Cs were satisfactory when used with molybdenum trioxide in the present invention to increase the yield of hydrocarbons containing from two to four carbon atoms. An average increase in yield of the desired hydrocarbons of about 50 percent was realized through the use of both components of the catalysts.

EXAMPLE 3

This example compares the effect of potassium carbonate loading on the selectivity of cobalt/-molybdenum catalysts. A quantity of commercially-available catalyst known as Ketjenfine 124-1, 5E LD (sold by the Armak Company) was impregnated with potassium carbonate (as detailed in the Apparatus and Procedure Section) to a level of 4 weight percent (calculated as $K_2O$). This catalyst is sold as a mixture of 4 weight percent cobalt oxide and 12 weight percent molybdenum trioxide on a support of alumina (80 weight percent). The apparatus of Example 1 was utilized. Reaction conditions are summarized below.

Temperature; 412° C.
Pressure; 315 psia
Volume Hourly Space Velocity; 256 hr$^{-1}$ The carbon monoxide conversion was found after several hours on stream to be 72 mole percent. The carbon monoxide conversion is defined as 100 times the moles of carbon monoxide converted divided by the moles of carbon monoxide in the feedstock. The reaction product consisted of:

$C_1$ Hydrocarbons; 36.6%
$C_2$ Hydrocarbons; 38.4%
$C_3$ Hydrocarbons; 17.3%
$C_4$ Hydrocarbons; 5.3%
$C_5$ Hydrocarbons; 2.2%

For comparison, note this example from the work of Schultz, Carn, and Anderson of the U.S. Bureau of Mines (full cite above). Run Z375 on page 18 of their report most nearly approximates the conditions herein employed. In that case an unsupported cobalt/molybdenum catalyst was used to react carbon monoxide and hydrogen under the following conditions:

Temperature; 300° C.
Volume Hourly Space Velocity; 300 hr$^{-1}$
$H_2$/CO Molar Ratio; 2
Analysis of the product revealed:
$C_1$ Hydrocarbons; 74.9%
$C_2$ Hydrocarbons; 12.4%
$C_3$ and $C_4$ Hydrocarbons; 9.9%
$C_5$ Hydrocarbons; 2.8%

Analysis of these data reveal a surprising and significant improvement in the yield of $C_2$ to $C_4$ hydrocarbons. The yield of this fraction rose from about 25 percent in the case of the Bureau of Mines work to about 63 percent in the case of the catalyst of the instant invention.

EXAMPLE 4

In the following runs which utilized the apparatus of Example 1 and the catalyst impregnation procedures of the Apparatus and Procedure Section, all variables where held constant except for the second component of the catalyst. The catalyst used in Run 4A included only components one and three. The catalyst was 11.15 weight percent tungsten trioxide on a support of saran carbon. The catalyst used in Run 4B was comprised of 10 weight percent tungsten trioxide and 4 weight percent potassium oxide on a Saran carbon support.

Reaction conditions for each run are summarized below:
Temperature; 400° C.
Volume Hourly Space Velocity; 300 hr$^{-1}$
Pressure; 300 psia
Analysis of the product revealed:

|  | Run 4A | Run 4B |
| --- | --- | --- |
| $C_1$ Hydrocarbons | 54.1 | 40.6 |
| $C_2$ Hydrocarbons | 28.6 | 40.5 |
| $C_3$ Hydrocarbons | 13.9 | 13.7 |
| $C_4$ Hydrocarbons | 2.7 | 5.2 |
| $C_5$ Hydrocarbons | 0.7 | 0 |

This example illustrates the significant increase (about 30 percent) in hydrocarbons containing two or more carbon atoms available through the invention while using tungsten as a component of the catalyst.

EXAMPLE 5

The following runs illustrate the use of nickel in the invention. The apparatus of Example 1 and the catalyst impregnation procedures of the Apparatus and Procedure Section were used. Runs 5A and 5B were conducted under the same reaction conditions. The catalyst used in Run 5A included only components one and three. The catalyst was 10 weight percent nickel oxide on a saran carbon support. The catalyst used in Run 5B was comprised of 10 weight percent nickel oxide and 4.6 weight percent potassium oxide on a saran carbon support.

Reaction conditions are summarized below:
Temperature; 388° C.
Volume Hourly Space Velocity; 300 hr$^{-1}$
Pressure; 300 psia
Analysis of the product revealed:

|  | Run 5A | Run 5B |
| --- | --- | --- |
| $C_1$ Hydrocarbons | 92.6 | 82.4 |
| $C_2$ Hydrocarbons | 5.7 | 13.1 |
| $C_3$ Hydrocarbons | 1.4 | 3.4 |
| $C_4$ Hydrocarbons | 0.3 | 1.1 |

Comparing the product analysis of the two runs, one notes the approximate 140 percent increase in the yield of hydrocarbons containing two or more carbon atoms available through the invention.

EXAMPLE 6

The following run was made with a catalyst of molybdenum trioxide and potassium oxide on alumina. Carbonyl sulfide was used to poison the catalyst to check the effect of hydrogen treatment upon activity and selectivity. Molybdenum trioxide and potassium oxide were impregnated on the alumina as in the Apparatus and Procedure Section. Levels of treatment were:
Weight percent $MoO_3$; 10
Weight percent $K_2O$; 4

The apparatus of Example 1 was used and reaction conditions are summarized below.
Temperature; 400° C.
Pressure; 300 psia
Volume Hourly Space Velocity; 300 hr$^{-1}$ Conversions and product distributions at various times during the run are summarized below.

| Time (Hours) | Carbon Monoxide Conversion (Mole Percent) | Product Hydrocarbon Distribution (Mole Percent) | | | | | |
| --- | --- | --- | --- | --- | --- | --- | --- |
| | | $C_1$ | $C_2$ | $C_3$ | $C_4$ | $C_5$ | $C_6$ |
| 11.2 | 35.7 | 34.6 | 22.3 | 24.4 | 12.3 | 3.2 | 3.2 |
| 12 | 100 ppm carbonyl sulfide was added to the feed on a continuous basis. | | | | | | |
| 85 | 20.9 | 47.2 | 18.1 | 26.3 | 8.4 | 0 | 0 |
| 85.1 | Carbonyl sulfide was eliminated from the feed The feed was interrupted to treat the catalyst with hydrogen at 600° C. for about sixteen hours. | | | | | | |
| 101 | Feed restored. | | | | | | |
| 121 | 32.6 | 53.2 | 20.6 | 17.0 | 9.2 | 0 | 0 |

These data show that carbonyl sulfide at 100 ppm adversely affects the activity and selectivity of molybdenum trioxide/potassium oxide on alumina. However, treatment of this catalyst with hydrogen for several hours restored its activity.

EXAMPLE 7

This run utilized molybdenum trioxide and potassium oxide with saran carbon beads as a support. Tested were the ability of the catalyst to resist sulfur poisoning and its ability to regain high activity and selectivity by treatment with hydrogen. The catalyst was impregnated according to the method detailed in the Apparatus and Procedure Section. It was tested in the apparatus of Example 1. Levels of treatment were:
Weight percent $MoO_3$; 11
Weight percent $K_2O$; 4

Reaction conditions are summarized below.
Temperature; 400° C.
Pressure; 295 psia
Volume Hourly Space Velocity; 300 hr$^{-1}$ Carbon monoxide conversions and product distributions at various times during the run are summarized below.

| Time (Hours) | Carbon Monoxide Conversion (Mole Percent) | Product Hydrocarbon Distribution (Mole Percent) | | | | | |
| --- | --- | --- | --- | --- | --- | --- | --- |
| | | $C_1$ | $C_2$ | $C_3$ | $C_4$ | $C_5$ | $C_6$ |
| 10 | 45 | 39.8 | 31.7 | 18.2 | 7.7 | 2.7 | 0 |
| 170 | 58 | 38.9 | 27.2 | 19.5 | 9.4 | 5.0 | 0 |
| 170.1 | 100 ppm carbonyl sulfide was added to the feed on a continuous basis. | | | | | | |
| 340 | 56 | 44.4 | 22.7 | 19.2 | 8.4 | 4.6 | 0.6 |
| 340.1 | Carbonyl sulfide was eliminated from the feed. The feed was interrupted to treat the catalyst with hydrogen at 500° for about sixteen hours. | | | | | | |
| 356 | Feed restored. | | | | | | |
| 359 | 61 | 39.6 | 25.7 | 20.3 | 7.8 | 4.7 | 2.0 |

These data show that the activity and selectivity of the catalyst prior to exposure to carbonyl sulfide can be restored by treatment with hydrogen at 500° C. for several hours.

EXAMPLE 8

To demonstrate the effect of carbonyl sulfide on a molybdenum trioxide/potassium oxide on alumina catalyst, the following run was made. Catalyst impregnation was done according to the Apparatus and Procedure Section and the apparatus of Example 1 was utilized. Levels of treatment were:

Weight percent $MoO_3$; 10
Weight percent $K_2O$; 2
Reaction conditions were as follows:
Temperature; 400° C.
Pressure; 295 psia
Volume Hourly Space Velocity; 300 $hr^{-1}$ Carbon monoxide conversions and product distributions at various times during the run are summarized below.

| Time (Hours) | Carbon Monoxide Conversion (Mole Percent) | Product Hydrocarbon Distribution (Mole Percent) | | | | | |
|---|---|---|---|---|---|---|---|
| | | $C_1$ | $C_2$ | $C_3$ | $C_4$ | $C_5$ | $C_6$ |
| 5 | 63 | 46.8 | 33.3 | 14.5 | 4.4 | 1.2 | 0 |
| 7 | Start introduction of 100 ppm carbonyl sulfide into feed on a continuous basis. | | | | | | |
| 97 | 48 | 63.0 | 25.4 | 9.7 | 2.0 | 0 | 0 |
| 97.1 | Elimination of carbonyl sulfide from the feed. Interruption of feed to treat the catalyst with hydrogen at 500° C. for about sixteen hours. | | | | | | |
| 123 | 57 | 60.0 | 27.6 | 10.1 | 2.3 | 0 | 0 |

These data show that the selectivity of the catalyst for producing hydrocarbons containing from two to four carbon atoms is adversely effected by the carbonyl sulfide. Treatment of the catalyst with hydrogen for several hours restored its activity as measured by the carbon monoxide conversion.

EXAMPLE 9

The following run was made to determine the rate of selectivity and activity loss caused by hydrogen sulfide to a saran carbon-supported potassium oxide/molybdenum trioxide catalyst and the effect of regeneration with hydrogen upon it. Molybdenum trioxide and potassium oxide were impregnated on saran carbon beads as detailed in the Apparatus and Procedure Section. The molybdenum trioxide was impregnated to a level of 9 weight percent and the potassium oxide, to a level of 5 weight percent. An apparatus was utilized which included in sequential order four high-pressure gas bottles, four automatic flow control valves, a manifold, a two-stage compressor, an electrically-heated tubular reactor, a heat exchanger, a flow meter, and a gas chromatograph. One of the bottles contained hydrogen. The second contained carbon monoxide. The third contained nitrogen. The fourth contained hydrogen doped with hydrogen sulfide as a sulfur impurity. Each bottle was independently connected through its own automatic flow control valve to the manifold. The manifold was connected to the inlet of the two-stage compressor. The discharge of the compressor was connected to the reactor. The reactor was constructed of 316 stainless steel, had a ¾ inch inside diameter, and a 21 inch bed length. The discharge of the reactor was connected to the heat exchanger. From the heat exchanger, the product was routed to the flow meter and then to the gas chromatograph.

Before each run, to reduce the catalyst, a stream of hydrogen from the high-pressure gas bottle was allowed to flow through the reactor maintained at 550° C. by means of the electric heaters for about sixteen hours. The temperature of the reactor was then increased to about 600° C. by means of the electric heaters and reduction continued for about sixteen more hours. The temperature was decreased to an operating range of about 400° C. in the presence of hydrogen. Then hydrogen and carbon monoxide were fed to the compressor from their respective gas bottles. A molar ratio of 1:1 and a volume hourly space velocity through the reactor of about 300 $hr^{-1}$ were accomplished by means of the automatic flow control valves. The compressor output was adjusted to about 935 psia. After a period of time sufficient to establish the performance of the catalyst, hydrogen supply was switched from the gas bottle containing pure hydrogen to the one containing hydrogen with hydrogen sulfide. After the effect on the catalyst of the hydrogen sulfide had been determined by reference to the carbon monoxide conversion and product hydrocarbon distribution, the bottles containing hydrogen with hydrogen sulfide and carbon monoxide were shut off. To regenerate the catalyst, pure hydrogen was allowed to flow for forty-eight hours through the reactor which had been heated to about 600° C. Then the temperature of the reactor was decreased to about 400° C. The flow from the hydrogen and carbon monoxide gas bottles was resumed at a 1:1 molar ratio and at a volume hourly space velocity of about 300 $hr^{-1}$. The discharge pressure of the compressor was adjusted to 935 psia. At the end of the run, the catalyst was cooled in the presence of hydrogen.

Carbon monoxide conversions and product distributions as a function of time are summarized in the following table.

| Time (Hours) | Carbon Monoxide Conversion (Mole Percent) | Product Hydrocarbon Distribution (Mole Percent) | | | | | |
|---|---|---|---|---|---|---|---|
| | | $C_1$ | $C_2$ | $C_3$ | $C_4$ | $C_5$ | $C_6$ |
| 357 | 82 | 37.7 | 30.0 | 19.5 | 7.3 | 3.8 | 1.8 |
| 706 | 78 | 35.5 | 28.8 | 19.2 | 8.3 | 4.5 | 3.5 |
| 706.1 | 68 ppm hydrogen sulfide was added to the feed on a continuous basis. | | | | | | |
| 759 | 22 | 56.1 | 26.1 | 12.7 | 2.5 | 0 | 2.6 |
| 759.1 | Hydrogen sulfide was eliminated from the feed. The feed was interrupted and the catalyst treated with hydrogen for about forty eight hours at 600° C. | | | | | | |
| 807 | Feed restored. | | | | | | |
| 814 | 83 | 27.5 | 30.7 | 23.3 | 8.3 | 5.2 | 5.0 |

This example illustrates that exposure of a molybdenum trioxide and potassium oxide on Saran carbon catalyst to sulfur impurities will adversely affect its activity and selectivity only temporarily if the exposure is followed by regeneration with hydrogen.

EXAMPLE 10

Fischer-Tropsch catalysts consisting of molybdenum disulfide promoted with minor proportions of an alkaline material are known (U.S. Pat. No. 2,490,488). However, these catalysts are taught to predominantly produce hydrocarbons of at least four carbon atoms and particularly hydrocarbons of at least five carbon atoms. To demonstrate the profound effect a support has upon the selectivity of such a catalyst, four different catalysts were prepared and then independently employed in a Fischer-Tropsch synthesis.

The first catalyst (Cat. #1) was singular $MoS_2$ (98 plus percent purity).

The second catalyst (Cat. #2) was singular $MoS_2$ deposited upon a coconut carbon support.

A third catalyst (Cat. #3) was prepared according to U.S. Pat. No. 2,490,488. $MoS_2$ powder (12.06 g) was admixed with crushed KOH pellets (0.39 g) to yield a catalyst composition consisting of 96.9 weight percent $MoS_2$ and 3.1 weight percent KOH.

A fourth catalyst (Cat. #4) was prepared by impregnating coconut carbon with $(NH_4)_2MoS_3$ and $K_2Co_3$. The impregnating solution of $(NH_4)_2MoS_3$ and $K_2Co_3$ was prepared by combining $(NH_4)_6Mo_7O_{24} \cdot 4H_2O$ (90.5 g) with $K_2Co_3$ (43.1 g), $(NH_4)_2S$ (503 g) and sufficient water to yield a 1000 ml solution. The catalyst composition analyzed as 11.5 weight percent $MoO_3$ and 4.8 weight percent $K_2O$.

(A) In the example of U.S. Pat. No. 2,490,488, an unsupported catalyst consisting of 97-98 weight percent $MoS_2$ and 2-3 weight percent KOH converted a CO and $H_2$ mixture (of an unspecified mole or weight ratio) at 530° F. (277° C.), 200 psig (13.6 atm) and an hourly space velocity (HSV) of 183 $hr^{-1}$ to a product comprising, in weight percent carbon in hydrocarbon product:

Methane & Ethane; 70
Propane; 1.5
Butane; 2.3
$C_5+$ ; 27.5

The CO conversion was 69 percent.

U.S. Pat. No. 2,490,488 does not report any results from a Fischer-Tropsch synthesis wherein a supported, alkaline-promoted $MoS_2$ catalyst was used.

(B) The third catalyst (96.9 weight percent $MoS_2$ and 3.1 weight percent KOH) was employed to convert a CO and $H_2$ mixture ($H_2$:CO volume ratio of 2.04:1) at 20.4 atm, 250° C. and an HSV of 100 $hr^{-1}$. The apparatus described hereinbefore was employed. No conversion products were detectable by gas chromatography (GC). The GC had a sensitivity of about 0.03 weight percent. It was necessary to use temperatures in excess of 316° C. (the maximum limit taught by U.S. Pat. No. 2,490,488) to obtain a measurable conversion.

(C) Part (B) was repeated except that both Cat. #1 and Cat. #3 were independently used at the following conditions:
$H_2$:CO volume ratio; 1.73:1
Pressure (atm); 19.4
Temperature (° C.); 400
HSV ($hr^{-1}$); 93
The results are reported below:

| Product Component | Catalyst | |
|---|---|---|
| | Cat. #1 | Cat. #3 |
| $C_1$ Hydrocarbons | 63.8 | 50.5 |
| $C_2$ Hydrocarbons | 23.2 | 21.4 |
| $C_3$ Hydrocarbons | 6.6 | 7.1 |
| $C_4$ Hydrocarbons | n.d.[1] | n.d.[1] |
| $C_5+$ Hydrocarbons | 6.4 | 30.0 |

[1]Not detectable.

CO conversion was 10.6 percent with $MoS_2$ and 9.6 percent with Cat. #1.

(D) Part (B) was again repeated except that both Cat. #2 and Cat. #4 were independently used at the following conditions:
$H_2$:CO volume ratio; 1.73:1
Pressure (atm); 19.4
Temperature (° C.); 360
HSV ($hr^{-1}$); 94
The results are reported below:

| Product Component | Catalyst | |
|---|---|---|
| | Cat. #2 | Cat. #4 |
| $C_1$ Hydrocarbons | 74.7 | 49.7 |
| $C_2$ Hydrocarbons | 20.8 | 27.5 |
| $C_3$ Hydrocarbons | 7.2 | 18.2 |
| $C_4$ Hydrocarbons | 1.3 | 4.6 |
| $C_5+$ Hydrocarbons | — | — |

CO conversion was 67.3 percent with Cat. #2 and 60.7 percent with Cat. #4.

(E) Part (B) was again repeated except that Cat. #1, Cat. #3 and Cat. #4 were independently used at the following conditions:
$H_2$:CO volume ratio; 0.75:1
Pressure (atm); 19.4
Temperature (° C.); 400
HSV ($hr^{-1}$); 162

| Product Component | Catalyst | | |
|---|---|---|---|
| | Cat. #1 | Cat. #3 | Cat. #4 |
| $C_1$ Hydrocarbons | 48.8 | 32.8 | 42.8 |
| $C_2$ Hydrocarbons | 26.9 | 21.0 | 33.2 |
| $C_3$ Hydrocarbons | 10.5 | 13.4 | 19.5 |
| $C_4$ Hydrocarbons | — | — | 4.5 |
| $C_5+$ Hydrocarbons | 13.8 | 32.9 | — |

CO conversion was 6.5 percent with Cat. #1, 34.4 percent with Cat. #4, and 4.9 percent with Cat. #3.

These reported data (B-E) demonstrate not only the profound effect a support has upon the selectivity of a $MoS_2$ catalyst (promoted with alkaline) but also its favorable effect upon its activity.

Although the invention has been described in considerable detail, it must be understood that such detail is for the purpose of illustration only and that many variations and modifications can be made by one skilled in the art without departing from the spirit and scope of the invention.

What is claimed is:

1. In a process for producing hydrocarbons by contacting carbon monoxide and hydrogen at reactive conditions, the improvement which comprises increasing the yield of the saturated and unsaturated hydrocarbons containing from two to four carbon atoms by contacting the carbon monoxide and hydrogen with a catalyst consisting of:

(A) between about 1 percent and about 95 percent by weight based upon the weight of the catalyst of at least one material selected from the group consisting of the metal, oxide or sulfide of molybdenum, tungsten, rhenium, ruthenium and platinum;

(B) between about 0.05 percent and about 50 percent by weight based upon the weight of the catalyst of at least one material selected from the group consisting of the hydroxide, oxide or salt of lithium, sodium, potassium, rubidium, cesium, magnesium, calcium, strontium, barium and thorium; and (C) at least about 1 percent by weight based upon the weight of the catalyst of a support.

2. The process of claim 1 wherein C is carbon, alumina, silica, zirconia, magnesia, or mixtures thereof.

3. The process of claim 1 wherein C is carbon or alumina.

4. The process of claim 1 wherein C is carbon.

5. The process of claim 1 wherein B is at least one material selected from the group consisting of the hydroxide, oxide or salt of lithium, sodium, potassium, rubidium and cesium.

6. The process of claim 1 wherein B is at least one material selected from the group consisting of the hydroxide, oxide or salt of potassium.

7. The process of claim 1 wherein C is present in an amount of at least about 50 percent by weight based upon the weight of the catalyst.

8. The process of claim 1 wherein C is present in an amount of at least about 80 percent by weight based upon the weight of the catalyst.

9. The process of claim 8 wherein A is present in an amount of at least about 10 percent by weight based upon the weight of the catalyst and B is present in a concentration of at least about 0.5 percent by weight based upon the weight of a catalyst.

10. The process of claim 9 wherein C is carbon, alumina, silica, zirconia, magnesia, or mixtures thereof.

11. The process of claim 9 wherein C is carbon or alumina.

12. The process of claim 9 wherein C is carbon.

13. The process of claim 9 wherein B is at least one material selected from the group consisting of the hydroxide, oxide or salt of lithium, sodium, potassium, rubidium and cesium.

14. The process of claim 9 wherein B is at least one material selected from the group consisting of the hydroxide, oxide or salt of potassium.

15. In a process for producing hydrocarbons by contacting carbon monoxide and hydrogen at reactive conditions, the improvement which comprises increasing the yield of the saturated and unsaturated hydrocarbons containing from 2 to 4 carbon atoms by contacting the carbon monoxide and hydrogen with a catalyst consisting of:
(A) between about 1 percent and about 95 percent by weight based upon the weight of the catalyst of at least one material selected from the group consisting of the metal, oxide or sulfide of molybdenum and tungsten;
(B) between about 0.05 percent and about 50 percent by weight based upon the weight of the catalyst of at least one material selected from the group consisting of the hydroxide, oxide or salt of lithium, sodium, potassium, rubidium, cesium, magnesium, calcium, strontium, barium and thorium; and
(C) at least about 1 percent by weight based upon the weight of the catalyst of a support.

16. The process of claim 15 wherein A is at least one material selected from the group consisting of the sulfide, oxide or metal of molybdenum.

17. The process of claim 15 wherein B is at least one material selected from the group consisting of the hydroxide, oxide or salt of lithium, sodium, potassium, rubidium and cesium.

18. The process of claim 17 wherein C is carbon, alumina, silica, zirconia, magnesia or mixtures thereof.

19. The process of claim 18 wherein A is at least one material selected from the group consisting of the sulfide, oxide or metal of molybdenum.

20. The process of claim 19 wherein B is at least one material selected from the group consisting of the hydroxide, oxide or salt of potassium.

21. The process of claim 20 wherein C is carbon or alumina.

22. The process of claim 21 wherein C is carbon.

23. In a process for producing hydrocarbons by contacting carbon monoxide and hydrogen at reactive conditions, the improvement which comprises increasing the yield of the saturated and unsaturated hydrocarbons containing from 2 to 4 carbon atoms by contacting the carbon monoxide and hydrogen with a catalyst consisting of:
(A) at least about 10 percent by weight based upon the weight of the catalyst of at least one material selected from the group consisting of the metal, oxide or sulfide of molybdenum and tungsten;
(B) at least about 0.5 percent by weight based upon the weight of the catalyst of at least one material selected from the group consisting of the hydroxide, oxide or salt of lithium, sodium, potassium, rubidium, cesium, magnesium, calcium, strontium, barium and thorium; and
(C) at least about 80 percent by weight based upon the weight of the catalyst of a support.

24. The process of claim 23 wherein A is at least one material selected from the group consisting of the sulfide, oxide or metal of molybdenum.

25. The process of claim 23 wherein B is at least one material selected from the group consisting of the hydroxide, oxide or salt of lithium, sodium, potassium, rubidium and cesium.

26. The process of claim 25 wherein C is carbon, alumina, silica, zirconia, magnesia, or mixtures thereof.

27. The process of claim 26 wherein A is at least one material selected from the group consisting of the sulfide, oxide or metal of molybdenum.

28. The process of claim 27 wherein B is at least one material selected from the group consisting of the hydroxide, oxide or salt of potassium.

29. The process of claim 28 wherein C is carbon or alumina.

30. The process of claim 28 wherein C is carbon.

* * * * *